United States Patent [19]

Libin

[11] Patent Number: 4,976,955

[45] Date of Patent: Dec. 11, 1990

[54] ORAL HYGIENE COMPOSITION

[76] Inventor: Barry M. Libin, 15 Thornhedge Rd., Bellport, N.Y. 11713

[21] Appl. No.: 491,726

[22] Filed: Mar. 12, 1990

Related U.S. Application Data

[63] Continuation-in-part of Ser. No. 438,803, Nov. 20, 1989.

[51] Int. Cl.$^5$ .................. A61K 9/20; A61K 33/40
[52] U.S. Cl. ............................ 424/53; 424/613
[58] Field of Search ............ 424/49, 53, 613, 614, 424/615, 616

[56] References Cited

U.S. PATENT DOCUMENTS

| | | | |
|---|---|---|---|
| 926,280 | 6/1909 | Morrison | 424/49 |
| 947,120 | 1/1910 | Morrison | 424/49 |
| 1,018,240 | 2/1912 | von Foregger | 424/53 |
| 1,536,305 | 5/1925 | Nitardy | 424/49 |
| 1,622,391 | 3/1927 | Nitardy et al. | 424/49 |
| 2,071,043 | 2/1937 | Nitardy | 424/53 |
| 3,577,521 | 5/1971 | Scheller et al. | 424/55 |
| 3,995,024 | 11/1976 | Hawking et al. | 424/55 |
| 4,223,003 | 9/1980 | Scheller | 424/53 |
| 4,346,493 | 8/1982 | Goudsmit | 424/49 |
| 4,837,008 | 6/1989 | Rudy et al. | 424/53 |
| 4,891,211 | 1/1990 | Winston | 424/53 |

FOREIGN PATENT DOCUMENTS

| | | | |
|---|---|---|---|
| 559142 | 6/1958 | Canada | 424/614 |
| 566586 | 11/1958 | Canada | 424/53 |
| 2643411 | 4/1977 | Fed. Rep. of Germany . | |
| 538522 | 8/1941 | United Kingdom | 424/53 |
| 723414 | 2/1955 | United Kingdom | 424/53 |
| 1209319 | 10/1970 | United Kingdom | 424/53 |

OTHER PUBLICATIONS

Volnov et al. Chem. Abstr. 66:59340b (1967).
Federov et al., Chem. Abstr. 81:54344f (1974).
Volnov et al., Chem. Abstr. 83:134393c (1975).
Goupil Chem. Abstr. 87:11477h (1977).
Ito et al., Chem. Abstr. 107:157660r (1987).

*Primary Examiner*—Shep K. Rose
*Attorney, Agent, or Firm*—Michael Ebert

[57] ABSTRACT

An oral hygiene composition that when brushed on or otherwise applied to the surface of teeth and adjacent gum tissue acts not only to bleach the teeth but also to improve the condition of the gums. The composition includes both magnesium peroxide and magnesium hydroxide, the magnesium peroxide, when activated, being capable of releasing active oxygen to effect a bleaching action removing stains from the teeth surfaces and to whiten and brighten them, and at the same time to oxidize and destroy anerobic bacteria associated with dental plaque. The magnesium hydroxide renders the pH of the magnesium peroxide alkaline, whereby the composition, when stored in a toothpaste tube or other sealed container remains inactive, and is activated only when the composition is applied orally and rendered acidic in the mouth by saliva.

9 Claims, No Drawings 4,976,955

ORAL HYGIENE COMPOSITION

RELATED APPLICATION

This application is a continuation-in-part of my copending application Ser. No. 438,803, filed Nov. 20, 1989, bearing the same title, the entire disclosure of which is incorporated herein by reference.

BACKGROUND OF INVENTION

1. Field of Invention

This invention relates generally to preparations for promoting sound oral hygiene, and more particularly to a storable, normally inactive composition which when applied onto the surface of teeth and adjacent gum tissues is then activated to carry out two functions, the first being cosmetic which is to whiten and brighten the teeth, the second being therapeutic which is to combat dental plaque and the resultant periodontal disease.

2. Status of Prior Art

In good part, the incidence of dental caries and periodontal disease can be imputed to the formation of plaque on the teeth. It has been reported in the literature that most of the world's population suffers from periodontal disease which is largely responsible for the loss of teeth.

Dental plaque is constituted by a thin layer of mucilaginous film which is subject to invasion by colonizing bacteria. Metabolic activity of these bacteria in the presence of dietary carbohydrates leads to the production of acetic and other acids. These acids attack soft gum tissue, thereby causing gingivitis; that is, the reddening and swelling of the normally pink guns, often accompanied by bleeding. These acids also react with the calcium of the teeth and the resultant decalcification of the organic matrix or dentin is such as to allow for the further invasion of bacteria and liquefying enzymes. Hence vital to sound oral hygiene is the reduction and control of dental plaque.

As noted in the Ng et al. U.S. Pat. No. 4,839,156 (1989), it has long been recognized that peroxy compounds such as hydrogen peroxide are effective against dental plaque, gingivitis, periodontitis and traumatic oral lesions. Hydrogen peroxide mouth rinses and other preparations inhibit the colonization and multiplication of the anerobic bacteria associated with dental plaque and periodontal disease. And because hydrogen peroxide functions as a bleaching agent, it will also act to whiten stained or discolored teeth, or normal teeth whose hard enamel surface has a somewhat yellowish or grayish tinge.

Most peroxy compounds tend to be unstable in storage, either because they are incompatible with other common ingredients included in the oral hygiene composition, or because they react with these ingredients. As a consequence, the composition loses its capacity to release active or nascent oxygen to attack the anerobic bacteria colonizing the plaque. To overcome this drawback, the Ng et al. patent provides a stable, aqueous, hydrogen peroxide gel.

Also concerned with the stability of hydrogen peroxide is the Winston et al. U.S. Pat. No. 4,812,308 (1989). To create a stable composition, this patent provides a tooth powder which is a mixture of sodium bicarbonate and sodium percarbonate. When this powder mixture makes contact with water, it releases active hydrogen peroxide.

Another approach to providing a stable hydrogen peroxide to combat periodontal disease is that taken in the Schaeffer U.S. Pat. No. 4,525,180 (1985) in which a hydrogen peroxide gel is stored in one compartment of a collapsible squeeze tube. Stored in the other compartment is a sodium bicarbonate paste which makes contact with the hydrogen peroxide gel only when the tube is squeezed.

The Clipper et al. U.S. Pat. No. 4,537,778 (1985) discloses an oral hygiene preparation in which hydrogen peroxide is combined with other ingredients with which this peroxide is compatible.

The Scheller U.S. Pat. No. 4,223,003 (1980) discloses a dentifrice which may be in paste or powder form and includes magnesium peroxide as an oxidizing agent for removing film from teeth. And the Smigel U.S. Pat. No. 4,405,559 (1982) discloses a dental paste that includes calcium peroxide and sodium perborate as oxidizing agents to remove stain and plaque from the teeth.

The use of hydrogen peroxide as an oxidizing agent to fight plaque and to remove stains present problems, for hydrogen peroxide is not only unstable and can quickly lose its efficacy, but it is also not free from toxicity and therefore may have adverse side effects if the dosage is excessive or its use is unduly prolonged. This is also true of other peroxy compounds such as sodium perborate.

Because a composition in accordance with the invention includes magnesium peroxide, the above-cited Clipper patent is of particular interest, for this 1985 patent indicates that it is known to use magnesium peroxide in an oral composition for prophylactic treatment with respect to caries, dental plaque, gingivitis and tooth stains. However, Clipper points out that magnesium peroxide "tends to be unstable in storage, continuously losing the capacity to release active nascent oxygen over relatively short periods of time." Clipper's preparation which has "enhanced stability in storage" includes hydrogen peroxide as the source of active oxygen. But for the reasons previously given, not only is hydrogen peroxide somewhat unstable, but it is not free from toxicity; hence a preparation of the Clipper type may have adverse effects.

SUMMARY OF INVENTION

In view of the foregoing, the main object of this invention is to provide a safe and effective oral hygiene composition which is inactive in storage and which when activated in use serves a dual function; the first being cosmetic to whiten and brighten the enamel of the teeth, the second being therapeutic to combat dental plaque which results in periodontal disease.

More particularly, an object of this invention is to provide a composition of the above type that is free of side effects, and which may be safely maintained on the teeth and the adjacent gun tissue.

Also an object of this invention is to provide an oral hygiene composition which after repeated applications will inhibit the activity of gingival pathogens and their toxic products to a degree imparting a healthier color, form and texture to the treated gingival tissue.

Briefly stated, these objects are attained in an oral hygiene composition that when brushed on or otherwise applied to the surface of teeth and adjacent gum tissue acts not only to bleach the teeth but also to improve the condition of the gums. The composition includes both magnesium peroxide and magnesium hydroxide, the magnesium peroxide, when activated, being capable of releasing active oxygen to effect a bleaching action removing stains from the tooth surfaces and to whiten and brighten them and at the same time to oxidize and destroy anerobic bacteria associated with dental plaque. The magnesium hydroxide renders the pH of the magnesium peroxide alkaline, whereby the composition when stored in a toothpaste tube or other sealed container remains inactive and is activated only when the composition is applied orally and rendered acidic in the mouth by saliva.

DETAILED DESCRIPTION OF INVENTION

An oral hygiene composition in accordance with the invention for releasing active oxygen is preferably in viscous paste form so that it may be brushed or otherwise applied to the surface of the teeth and to adjacent gingival tissue so as to create a removable layer adherent thereto. This layer is permitted to remain on the surfaces for several minutes, during which time active oxygen is released to bleach the enamel of the teeth and at the same time to oxidize and destroy anerobic bacteria associated with dental plaque.

The following are the ingredients of this composition whose viscosity may be adjusted in a range extending from a moderately heavy cream to a thick paste.

| Ingredient | Percentage by Weight |
| --- | --- |
| A. magnesium peroxide (bleaching, oxidizing and germicidal agent) | from 0.5% to 10% |
| B. magnesium hydroxide (pH adjuster for the magnesium peroxide in an amount to render the pH alkaline. | from 0.5% to 10% |
| C. calcium carbonate (cleansing agent) | from 5% to 20% |
| D. sodium carboxyl methyl cellulose (thickening agent) | from 0.5% to 10% |
| E. glycerine (gelling agent) | from 5% to 20% |
| F. de-ionized water (in an amount to confer a suitable wetness to the cream or paste in accordance with its desired viscosity) | from 0.5% to 40% |
| G. dicalcium phosphate (cleansing agent) | from 0.5% to 10% |
| H. sorbitol (this acts as a humectant to retain moisture in the composition) | from 10% to 70% |
| I. magnesium carbonate (cleansing agent) | from 0.5% to 10% |
| J. magnesium oxide (cleansing agent) | from 0.5% to 10% |
| K. sodium lauryl sulfate (anionic surfactant having detergent and foaming properties) | from 0.5% to 10% |
| L. peppermint oil (flavoring agent) | from 0.1% to 5% |

Magnesium peroxide is virtually insoluble in water. However, when slurried in water, partial hydrolysis takes place with a slow release of active oxygen. This release of active oxygen acts to oxidize and thereby bleach the enamel surface of the teeth and at the same time treat the adjacent gingival tissue.

Whitening and brightening is but one function of the oral hygiene composition, for it also serves therapeutically as an oxidizing germicidal or anti-microbial agent to combat anerobic bacteria lodged in plaque, and in doing so to arrest periodontal disease. Because this treatment is repeated each time the teeth are brushed and the composition permitted to remain thereon for several minutes or longer, at the end of each treatment, there is a perceptible improvement in the condition of the gum tissue. And with repeated treatments (several times a day), the gum tissue will be restored to its normal healthy, pink, firm condition. The composition, while it includes to a small degree abrasive constituents, allows for long term brushing of the teeth without inflicting damage to the enamel surfaces.

In preparing the composition, first the glycerine (E), the de-ionized water (F), the sodium carboxylmethyl cellulose (D) and the sorbitol (H) are intermingled to produce a gel of the desired consistency, after which the other ingredients are stirred into the gel to complete the composition.

It is important to note that the prepared composition is non-acidic or alkaline; that is, it has a pH of 8 or higher. Preferably, the pH is in a range of about 9.5 to 11.0. In this alkaline state, the composition is inactive and stable, and may be stored in a squeeze tube or other suitable sealed container. When, however, the composition is applied orally, it is rendered acidic by the saliva in the mouth, and only then does it proceed to release active oxygen.

It is to be noted that the composition includes a relatively small amount of de-ionized water as compared to the amount disclosed in my co-pending application. The reason for this small amount is that while magnesium peroxide is virtually insoluble in water, some interaction may occur after prolonged storage, resulting in the release of active oxygen. As a consequence, the composition may be in a weakened condition when put to use orally. The relatively small amount of water included in the composition extends its effective shelf life.

While there has been disclosed a preferred composition, it is to be understood that changes may be made therein without departing from the invention. Thus gelling and thickening agents other than those disclosed herein may be used, and other forms of sweeteners and flavoring agents may be employed in the composition.

I claim:

1. A normally inactive and storable wet aqueous alkaline cream or paste oral hygiene composition which when the composition is applied to the surface of the teeth and adjacent gingival tissue, it then interacts with saliva in the mouth and is rendered active, said composition consisting essentially of from 0.5% to 40% by weight of de-ionized water, in an amount effective to confer wetness to the cream or paste containing:
    (a) magnesium peroxide; and
    (b) magnesium hydroxide in an amount relative to the magnesium peroxide sufficient to impart alkalinity to the composition to render it inactive and storable, said composition when applied then interacting with said saliva which imparts acidity thereto, thereby activating the composition, and causing the magnesium peroxide to release active oxygen to effect whitening of the teeth surfaces and acting to destroy anerobic bacteria associated with dental plaque.

2. A composition as set forth in claim 1, wherein the amount of magnesium hydroxide is such as to produce alkalinity with a pH in excess of 8.

3. A composition as set forth in claim 2, wherein said pH lies in a range of about 9.5 to 11.0.

4. A composition as set forth in claim 1, further including a thickening agent and a gelling agent in an amount producing a toothpaste.

5. A composition as set forth in claim 4, wherein said thickening agent is sodium carboxymethyl cellulose.

6. A composition as set forth in claim 4, wherein said gelling agent is glycerine.

7. A composition as set forth in claim 1, further including sorbitol functioning as a humectant to retain moisture in the composition.

8. A composition as set forth in claim 1, further including sodium lauryl sulfate as a detergent and foaming agent.

9. A composition as set forth in claim 1 in which the composition is in extrudable paste form and is stored in a toothpaste tube.

* * * * *